US006487446B1

(12) United States Patent
Hill et al.

(10) Patent No.: US 6,487,446 B1
(45) Date of Patent: Nov. 26, 2002

(54) METHOD AND SYSTEM FOR SPINAL CORD STIMULATION PRIOR TO AND DURING A MEDICAL PROCEDURE

(75) Inventors: Michael R.S. Hill, Minneapolis, MN (US); Scott E. Jahns, Hudson, WI (US); James R. Keogh, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 115 days.

(21) Appl. No.: 09/669,960

(22) Filed: Sep. 26, 2000

(51) Int. Cl.[7] .............................. A61N 1/30; A61N 1/18
(52) U.S. Cl. ............................. 604/20; 607/9; 607/117
(58) Field of Search .............................. 607/5, 9, 117; 604/20

(56) References Cited

U.S. PATENT DOCUMENTS

| | | |
|---|---|---|
| 4,304,239 A | 12/1981 | Perlin |
| 4,640,298 A | 2/1987 | Pless et al. |
| 4,671,295 A | 6/1987 | Abrams et al. |
| 4,722,347 A | 2/1988 | Abrams et al. |
| 4,753,244 A | 6/1988 | Landymore et al. |
| 4,960,133 A | 10/1990 | Hewson |
| 5,014,698 A | 5/1991 | Cohen |
| 5,024,228 A | 6/1991 | Goldstone et al. |
| 5,044,367 A | 9/1991 | Endres et al. |
| 5,052,390 A | 10/1991 | Hewson |

(List continued on next page.)

FOREIGN PATENT DOCUMENTS

| | | |
|---|---|---|
| DE | 28 11 325 | 9/1979 |
| EP | 0 589 252 | 3/1994 |
| WO | 92/11064 | 7/1992 |
| WO | 97/40885 | 11/1997 |
| WO | WO 99/09971 | 8/1998 |
| WO | WO 99/09973 | 8/1998 |
| WO | 99/07354 | 2/1999 |
| WO | 01/00273 | 1/2001 |

OTHER PUBLICATIONS

US 6,184,239, 2/2001, Puskas (withdrawn)
An article entitled "Coronary artery surgery with induced temporary asystole and intermittent ventricular pacing: an experimental study" by R. Khanna and H.C. Cullen, dated Apr. 1996, taken from *Cardiovascular Surgery*, vol. 4, No. 2, pp. 231–236.
An unnamed editorial by Adrian R. M. Upton, dated Oct. 1992, taken from *PACE* vol. 15, pp. 1543–1544.
An article entitled "Selective Stimulation of Parasympathetic Nerve Fibers to the Human Sinoatrial Node," by Mark D. Carlson, Alexander S. Geha, Jack Hsu, Paul J. Martin, Matthew N. Levy, Gretta Jacobs and Albert J. Waldo, dated Apr. 1992, taken from *Circulation* vol. 85, No. 4, pp. 1311–1317.
An article entitled "Controlled Intermittent Asystole: Pharmacologic Potentiation of Vagal–Induced Asystole," by Bradley L. Bufkin, John D. Puskas, Jakob Vinten–Johansen, Steven T. Shearer, and Robert A. Guyton, dated 1998, published by The Society of Thoracic Surgeons, 6 pages.

(List continued on next page.)

*Primary Examiner*—William Wayner
(74) *Attorney, Agent, or Firm*—Thomas G. Berry; Daniel W. Latham

(57) ABSTRACT

A method of performing a medical procedure, such as surgery, is provided. The spinal cord is stimulated in order to control at least one physiological function. The medical procedure is performed and stimulation of the spinal cord is stopped.

14 Claims, 4 Drawing Sheets

U.S. PATENT DOCUMENTS

| | | |
|---|---|---|
| 5,056,519 A | 10/1991 | Vince |
| 5,056,532 A | 10/1991 | Hull et al. |
| 5,125,406 A | 6/1992 | Goldstone et al. |
| 5,127,407 A | 7/1992 | Tan .......................... 356/41 X |
| 5,129,392 A | 7/1992 | Bardy et al. |
| 5,156,149 A | 10/1992 | Hudrlik |
| 5,199,428 A | 4/1993 | Obel et al. |
| 5,203,326 A | 4/1993 | Collins ................. 128/419 PG |
| 5,243,980 A | 9/1993 | Mehra ........................... 607/6 |
| 5,265,603 A | 11/1993 | Hudrlik ......................... 607/9 |
| 5,284,146 A | 2/1994 | Czar et al. ............... 604/175.1 |
| 5,292,338 A | 3/1994 | Bardy ........................... 607/5 |
| 5,330,507 A | 7/1994 | Schwartz ..................... 607/14 |
| 5,330,515 A | 7/1994 | Rutecki et al. ............... 607/46 |
| 5,334,221 A | 8/1994 | Bardy |
| 5,354,318 A | 10/1994 | Taepke ........................ 607/22 |
| 5,356,425 A | 10/1994 | Bardy et al. ................ 607/141 |
| 5,403,356 A | 4/1995 | Hill et al. ..................... 607/14 |
| 5,411,529 A | 5/1995 | Hudrlik ......................... 607/6 |
| 5,501,703 A | 3/1996 | Holsheimer et al. .......... 407/46 |
| 5,507,784 A | 4/1996 | Hill et al. ..................... 607/14 |
| 5,540,730 A | 7/1996 | Terry, Jr. et al. .............. 607/40 |
| 5,540,732 A | 7/1996 | Testerman ................... 607/42 |
| 5,549,655 A | 8/1996 | Erickson ..................... 607/42 |
| 5,571,150 A | 11/1996 | Wernicke et al. ............. 607/72 |
| 5,578,061 A | 11/1996 | Stroetmann et al. ........... 607/4 |
| 5,611,350 A | 3/1997 | John ........................ 607/45 X |
| 5,620,468 A | 4/1997 | Mongeon et al. .............. 607/5 |
| 5,651,378 A | 7/1997 | Matheny et al. ............ 607/9 X |
| 5,690,681 A | 11/1997 | Geddes et al. .................. 607/4 |
| 5,700,282 A | 12/1997 | Zabara ......................... 607/9 |
| 5,792,187 A | 8/1998 | Adams .......................... 607/5 |
| 5,799,661 A | 9/1998 | Boyd et al. ............... 604/49 X |
| 5,836,994 A | 11/1998 | Bourgeois .................... 607/40 |
| 5,913,876 A | 6/1999 | Taylor et al. ................... 607/2 |
| 5,916,239 A | 6/1999 | Geddes et al. ................ 607/14 |
| 5,928,272 A | 7/1999 | Adkins et al. ................ 607/45 |
| 5,964,789 A | 10/1999 | Karsdon ...................... 607/39 |
| 5,995,872 A | 11/1999 | Bourgeois .................... 607/40 |
| 6,006,134 A | 12/1999 | Hill et al. ...................... 607/9 |
| 6,043,273 A | 3/2000 | Duhaylongsod ............. 514/478 |
| 6,060,454 A | 5/2000 | Duhaylongsod ............. 514/26 |
| 6,073,048 A | 6/2000 | Kieval et al. .................. 607/17 |
| 6,087,394 A | 7/2000 | Duhaylongsod ............ 514/478 |
| 6,101,412 A | 8/2000 | Duhaylongsod ............... 607/2 |
| 6,127,410 A | 10/2000 | Duhaylongsod ............ 514/478 |
| 6,141,589 A | 10/2000 | Duhaylongsod ............. 607/10 |
| 6,266,564 B1 * | 7/2001 | Hill et al. ....................... 607/9 |

OTHER PUBLICATIONS

A presentation summary entitled "Controlled Ventricular Asystole with Surgeon–Actuated Pacing For Off–Pump Coronary Artery Bypass Grafting: A Proposed Surgical Method," by Francis G. Duhaylongsod and William R. Burfeind, Jr., dated Jun. 25, 1998, 1 page.

An article entitled "Age–Related Changes of Cardiac Control Function in Man," by Iwao Sato, Yasuhiro Hasegawa, Norikazu Takahashi, Yukio Hirata, Katsuro Shimomura, and Ken Hotta, dated 1981, taken from *Journal of Gerontology* vol. 36, No. 5, pp. 564–572.

An article entitled "Cardiac Muscarinic Receptors Decrease with Age In Vitro and in Vivo Studies," by Otto–Erich Brodde, Ulrich Konschak, Karin Becker, Florian Ruter, Ulrike Poller, Jens Jakubetz, Joachim Radke, and Hans–Reinhard Zerkowski, dated Jan. 1998, taken from the *Journal of Clinical Investigation*, vol. 101, No. 2, pp. 471–478.

An article entitled "Age–Dependent Changes in Cardiac Muscarinic Receptor Function in Healthy Volunteers" by Ulrike Poller, Gesine Nedelka, Joachim Radke, Klaus–Ponicke, and Otto–Erich Brodde, dated Jan. 1997, taken from the *Journal of the American College of Cardiology* vol. 29, No. 1, pp. 187–193.

An article entitled "Age–Related Changes of Cardiac Parasympathetic Modulation After Vasovagal Syncope," by Alfonso Lagi, Simone Cencetti, Lamberto Fattorini, and Carlo Tamburini, dated Mar. 15, 1999, taken from the *American Journal of Cardiology* vol. 83, pp. 977–980.

An article entitled "Desensitization of the choloinergic receptor at the sinoatrial cell of the kitten," by Jose Jalife, Allan J. Hamilton, and Gordon K. Moe, dated 1980, published by the American Physiological Society, pp. H439–448.

An article entitled "Sensitivity differences of SA and AV node to vagal stimulation: attenuation of vagal effects at SA node" by Jerod M. Loeb, Daniel P. Dalton, and John M. Moran, dated 1981, published by the American Physiological Society, pp. H684–690.

An article entitled "Vagal Nerve Monitoring: A Comparison of Techniques in a Canine Model" by Mark A. Severtson, John P. Leonetti and Denise Jarocki, dated 1997, taken from the *American Journal of Otology*, pp. 398–400.

A short note entitled "The NIM–2 nerve integrity monitor in thyroid and parathyroid surgery" by J. Barwell, J. Lytle, R. Page, and D. Wilkins, dated 1997, taken from the *British Journal of Surgery* vol. 84, No. 854, pp. 854.

An article entitled "A New Method for Intraoperative Recurrent Laryngeal Nerve Monitoring" by Richard W. Maloney, Benjamin W. Murcek, Kirk W. Steehler, Dennis Sibly, and Richard E. Maloney, dated Jan. 1994, taken from the *ENT Journal* vol. 73, No. 1, pp. 30–33.

An article entitled "Revision and Removal of Stimulating Electrodes Following Long–Term Therapy with the Vagus Nerve Stimulator" by Jose Espinosa, Mary Aiello, and Dean Naritoku, dated 1999, taken from *Surgical Neurology*, vol. 51, pp. 659–664.

An article entitled "Epilepsy, Vagal Nerve Stimulation by the NCP System, All–Cause Mortality, and Sudden, Unexpected, Unexplained Death" by J. F. Annegers, Sharon P. Coan, W. A. Hauser, and J. Leestma, dated 2000, taken from *Epilepsia* vol. 41, No. 5, pp. 549–553.

An article entitled "Fade of cardiac responses during tonic vagal stimulation" by Paul Martin, Matthew N. Levy, and Yasuo Matsuda, copyright 1982, published by the American Physiological Society, pp. H219–225.

A presentation transcript entitled "Techniques of Stabilization" presented by Robert G. Matheny at a conference entitled "Experiences in Minimally Invasive Surgery," Minneapolis, Jun. 19–21, 1997, 6 pages.

A presentation transcript entitled "Vagus Nerve Stimulation as a Method to Temporarily Slow or Arrest the Heart" presented by Robert G. Matheny and Carl J. Shaar at the Second Utrecht MICABG Workshop, Utrecht, Netherlands, Oct. 4–5, 1996, 2 pages.

An article entitled "Vagus Nerve Stimulation of Treatment of Partial Seizures: 1. A Controlled Study of Effect on Seizures" by E. Ben–Menachem, R. Manon–Espaillat, R. Ristanovic, B. J. Wilder, H. Stefan, W. Mirza, W. B. Tarver, J. F. Wernicke, and the First International Vagus Nerve Study Group, dated 1994, taken from *Epilepsia* vol. 35, No. 3, pp. 616–626.

An article entitled "Vagus Nerve Stimulation for Treatment of Partial Seizures: 2. Safety, Side Effects, and Tolerability" by R. E. Ramsay, B. M. Uthman, L. E. Augustinsson, A. R. M. Upton, D. Naritoku, J. Willis, T. Treig, G. Barolat, J. F. Wernicke, and the First International Vagus Nerve Stimulation Study Group, dated 1994, taken from *Epilepsia* vol. 35, No. 3, pp. 627–636.

An article entitled "Vagus Nerve Stimulation for Treatment of Partial Seizures: 3. Long–Term Follow–Up on First 67 Patients Exiting a Controlled Study" by R. George, M. Salinsky, R. Kuzniecky, W. Rosenfeld, D. Bergen, W. B. Tarver, J. F. Wernicke, and the First International Vagus Nerve Stimulation Study Group, dated 1994, taken from *Epilepsia* vol. 35, No. 3, pp. 637–643.

Conference proceedings entitled "Vagus Nerve Stimulation for the Control of Epilepsy," edited by B. J. Wilder, dated 1990, taken from *Epilepsia* vol. 31, Supplement 2, pp. S1–60.

An article entitled "Carotid Sinus Nerve Stimulation in The Treatment of Angina Pectoris and Supraventricular Tachycardia" [Authors Eugene Braunwald, M.D., Stephen F. Vatner, M.D., Nina S. Braunwald, M.D., Burton E. Sobel, M.D., taken from California Medicine:The Western Journal of Medicine, San Diego, From the Departments of Medicine and Surgery, University of California, San Diego, School of Medicine, La Jolla, dated Mar. 1970, pp. 41–50].

An article entitled "Functional Anatomy of the Cardiac Efferent Innervation" [Authors W.C. Randall and J.L. Ardell, taken from Neurocardiology, Mount Kisco, NY, Future Publishing Co, dated 1988, pp. 3–24].

An article entitled "Neural Effects on Sinus Rate and Atrioventricular Conduction Produced by Electrical Stimulation from a Trnsvenous Electrode Catheter in the Canine Right Pulmonary Artery" [Authors Terry B. Cooper, Gilbert R. Hageman, Thomas N. James, and Albert L. Waldo, taken from Circulation Research, vol. 46, No. 1, dated Jan. 1980, pp. 48–57].

An article entitled "Parasympathetic Postganglionic Pathways to the Sinoartrial Node" [Authors K.M. Bluemel, R.D. Wurster, W.C. Randall, M.J. Duff and M.F. O'Toole, copyright 1990 by the American Physiological Society, pp. H1504–H1510].

An article entitled "'Vagal Tuning' A New Concept in the Treatment of Supraventricular Arrhythmias, Angina Pectoris, and Heart Failure" [Authors Aydin M. Bilgutay, MD, Ilhan M. Bilgutay, B.E.E., Frederick K. Merkel, MD, and C. Walton Lillehel, PhD, MD, taken from Journal of Thoracic and Cardiovascular Surgery, vol. 56, No. 1, published by Department of Surgery, University of Minnesota Medical Center, Minneapolis, MN, dated 6/68, pp. 71–82].

* cited by examiner

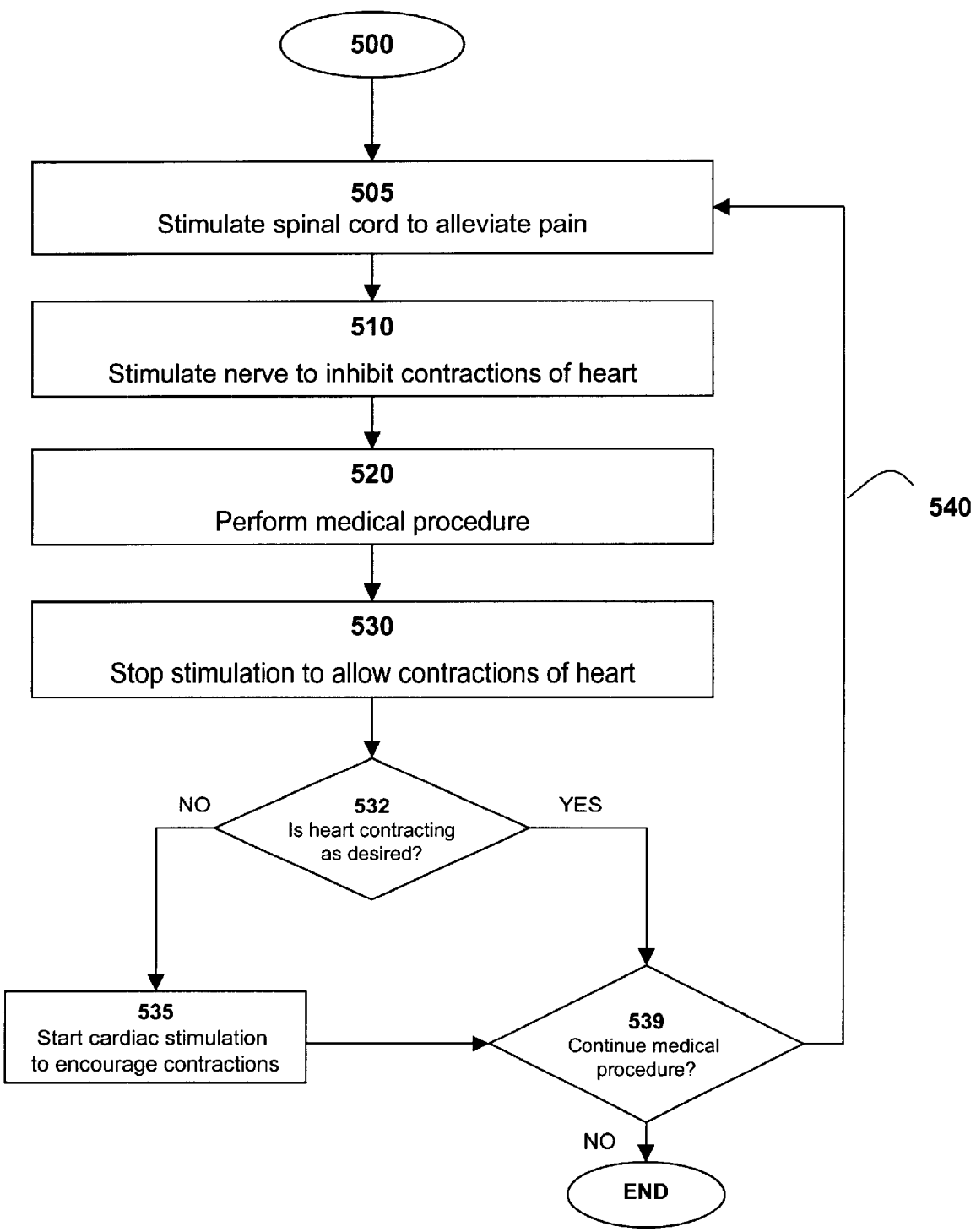

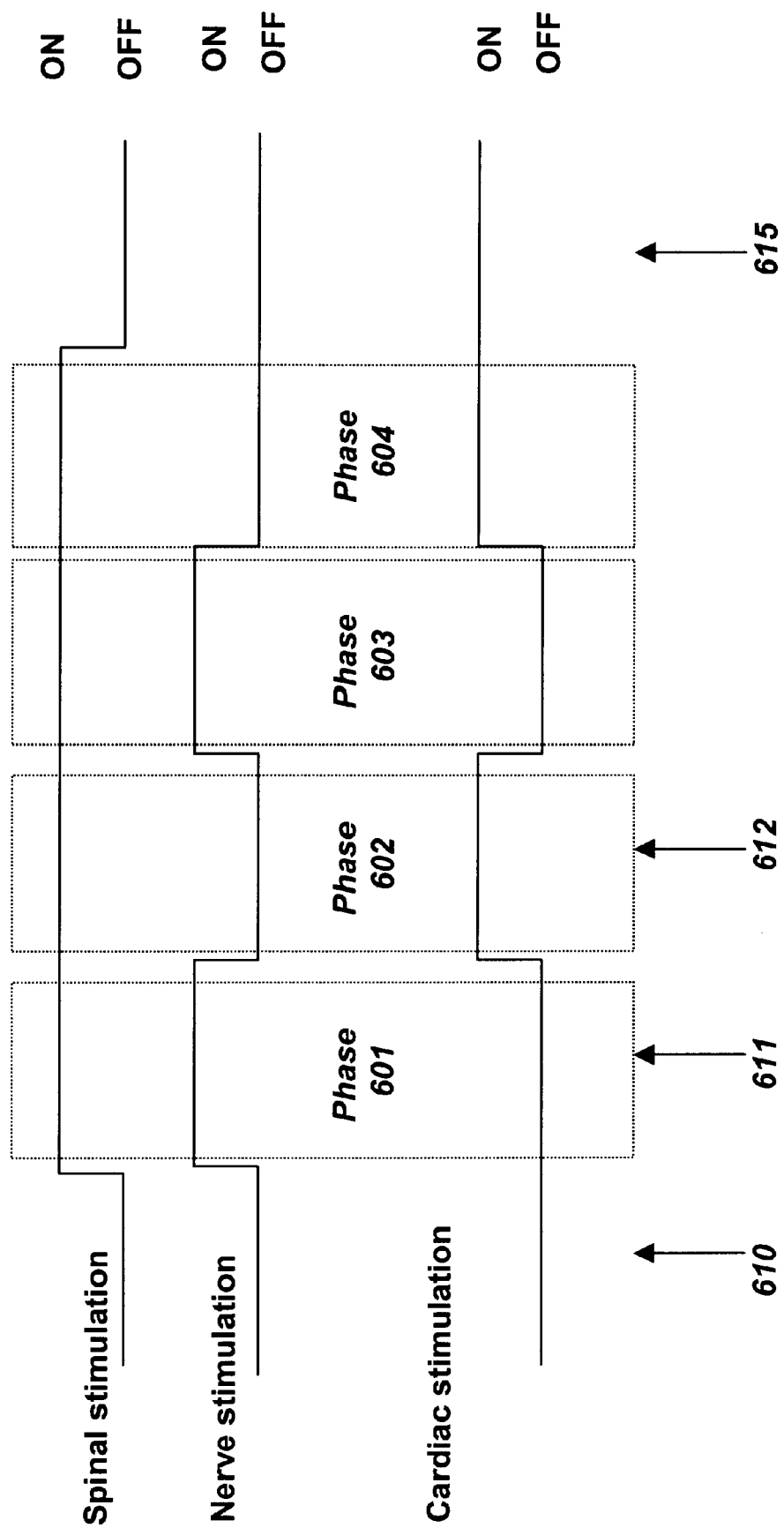

METHOD AND SYSTEM FOR SPINAL CORD STIMULATION PRIOR TO AND DURING A MEDICAL PROCEDURE

FIELD OF THE INVENTION

This invention relates to methods for performing a medical procedure, especially a procedure during which it is desirable to provide stimulation to the spinal column. More particularly, this invention relates to methods and systems of stimulating the spinal cord during a medical procedure in which the beating of a heart is modified to allow the procedure to be performed or to allow blood flow to be controlled.

BACKGROUND OF THE INVENTION

Stimulation of the spinal cord can result in control of motor responses, nerve responses and other organ functions. For example, stimulation of the spinal cord in one area may control the function of the bladder. Stimulation of the spinal cord at yet another area may control the patient's ability to feel pain.

In a typical medical procedure, it may be desirable to stimulate the spinal cord in order to control the function of an organ. In particular, medical procedures in which the flow of blood is controlled, usually by stopping the heart, may benefit from using stimulation of the spinal cord to reduce pain.

Currently, stimulation of the spinal cord is used to control the functions of organs, the responses of organs and the responses of nerves in the context of post surgical treatment. That is, a spinal cord stimulator may be inserted in the spine to control pain after a surgical procedure has been done.

It would be desirable therefore to stimulate the spinal cord during a medical procedure to control the function of one or more organs.

It would further be desirable to stimulate the spinal cord to ease pain during a medical procedure.

SUMMARY OF THE INVENTION

One aspect of the present invention provides a method of performing a medical procedure. A spinal cord is stimulated to control at least one physiological function. The medical procedure is performed. Stimulation of the spinal cord is then stopped. The physiological function may be a function of the lungs or the heart. The physiological function may also be the reduction of pain.

Stimulation of the cord may be intermittent. Drugs, such as a beta-blocker, a cholinergic agent, a cholinesterase inhibitor, a calcium channel blocker, a sodium channel blocker, a potassium channel agent, adenosine, an adenosine receptor agonist, an adenosine deaminase inhibitor, dipyridamole, a monoamine oxidase inhibitor, digoxin, digitalis, lignocaine, a bradykinin agent, a serotoninergic agonist, an antiarrythmic agent, a cardiac glycoside, a local anesthetic, atropine, a calcium solution, an agent that promotes heart rate, an agent that promotes heart contractions, dopamine, a catecholamine, an inotrope glucagon, a hormone, forskolin, epinephrine, norepinephrine, thyroid hormone, a phosphodiesterase inhibitor, prostacyclin, prostaglandin and a methylxanthine, may be delivered during the procedure. These drugs may be naturally occurring or chemically synthesized.

The medical procedure may be one of the following: surgical procedures, non-surgical procedures, endoscopic procedures, fluoroscopic procedures, stent delivery procedures, aortic aneurysm repairs, cranial aneurysm repairs, delivery of drugs, delivery of biological agents, cardiac surgery with cardiopulmonary bypass circuits, cardiac surgery without cardiopulmonary bypass circuits, brain surgery, cardiograms, heart valve repair, heart valve replacement, MAZE procedures, revascularization procedures, transmyocardial revascularization, percutaneous myocardial revascularization, CABG procedures, anastomosis procedures, beating heart surgery, vascular surgery, neurosurgery, brain surgery, electrophysiology procedures, diagnostic procedures, therapeutic procedures, ablation procedures, ablation of arrhythmias, endovascular procedures, treatment of the liver, treatment of the spleen, treatment of the heart, treatment of the lungs, treatment of major blood vessels; non-invasive procedures, invasive procedures, port-access procedures, imaging procedures, CAT scan procedures, MRI procedures, gene therapy procedures, cellular therapy procedures, cancer therapy procedures, radiation therapy procedures, transplantation procedures, coronary angioplasty procedures, atherectomy procedures, atherosclerotic plaque removal procedures and birthing procedures. The spinal cord may be accessed via intrathecal access, epidural access, and transcutaneous access.

Another aspect of the present invention provides a system for performing a medical procedure. The system includes a spinal stimulator to reduce pain during the medical procedure, a nerve stimulator in communication with the spinal stimulator to inhibit beating of the heart; and a cardiac stimulator in communication with the spinal stimulator to stimulate beating of the heart. The system may also include drug delivery means for delivering at least one drug during the medical procedure such as a spray, a cream, an ointment, a medicament, a pill, a patch, a catheter, a cannula, a needle and syringe, a pump, and an iontophoretic drug delivery device. The nerve stimulator may stimulate vagus nerve fibers, hypoglossal nerve fibers, phrenic nerve fibers, parasympathetic nerve fibers, and sympathetic nerve fibers, a vagal nerve, a carotid sinus nerve, a fat pad. The spinal stimulator comprises one or more electrodes such as spinal stimulation electrodes, balloon-type electrodes, basket-type electrodes, umbrella-type electrodes, suction-type electrodes, guided catheters, guided electrodes, steerable catheters, and steerable electrodes. The nerve stimulator also comprises one or more electrodes such as nerve stimulation electrodes, endotracheal electrodes, endoesophageal electrodes, intravascular electrodes, transcutaneous electrodes, intracutaneous electrodes, balloon-type electrodes, basket-type electrodes, umbrella-type electrodes, tape-type electrodes, suction-type electrodes, screw-type electrodes, barb-type electrodes, bipolar electrodes, monopolar electrodes, metal electrodes, wire electrodes, patch electrodes, cuff electrodes, clip electrodes, needle electrodes and probe electrodes. The cardiac stimulator also comprises one or more electrodes such as cardiac stimulation electrodes, clip electrodes, needle electrodes, probe electrodes, pacing electrodes, epicardial electrodes, patch electrodes, intravascular electrodes, balloon-type electrodes, basket-type electrodes, tape-type electrodes, umbrella-type electrodes, suction-type electrodes, endotracheal electrodes, endoesophageal electrodes, transcutaneous electrodes, intracutaneous electrodes, screw-type electrodes, barb-type electrodes, bipolar electrodes, monopolar electrodes, metal electrodes, wire electrodes and cuff electrodes.

Another aspect of the present invention provides a method of performing heart surgery. A spinal cord is stimulated to control pain. A nerve is stimulated to reduce the beating of a heart. The heart is operated upon. Stimulation of the nerve is reduced or stopped. The heart is stimulated to cause it to beat. The nerve is restimulated to re-inhibit beating of the heart and the surgery is continued.

Another aspect of the present invention provides a device for controlling pain during a medical procedure. The device includes a processor connected to a spinal stimulation electrode and a nerve stimulation electrode. The processor processes output from the spinal stimulation electrode and adjusts output from the nerve stimulation electrode based on output from the spinal stimulation electrode. The device may also include a cardiac stimulation electrode operatively connected to the processor, wherein the processor processes output from the spinal stimulation electrode and adjusts output from the cardiac stimulation electrode based on output from the spinal stimulation electrode.

Another aspect of the present invention provides a method of delivering a baby. The spinal cord is stimulated to control pain. The baby is delivered. Then stimulation of the spinal cord is stopped.

The foregoing, and other, features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims in equivalence thereof.

BRIEF DESCRIPTION OF THE DRAWINGS

FIG. 3 is a flow diagram of one embodiment of a method of performing a medical procedure in accordance with the present invention; and FIG. 4 is a timeline view of one embodiment of a system for stimulating the spinal cord during a medical procedure in accordance with the present invention.

DETAILED DESCRIPTION OF THE PRESENTLY PREFERRED EMBODIMENTS

Figure 1:
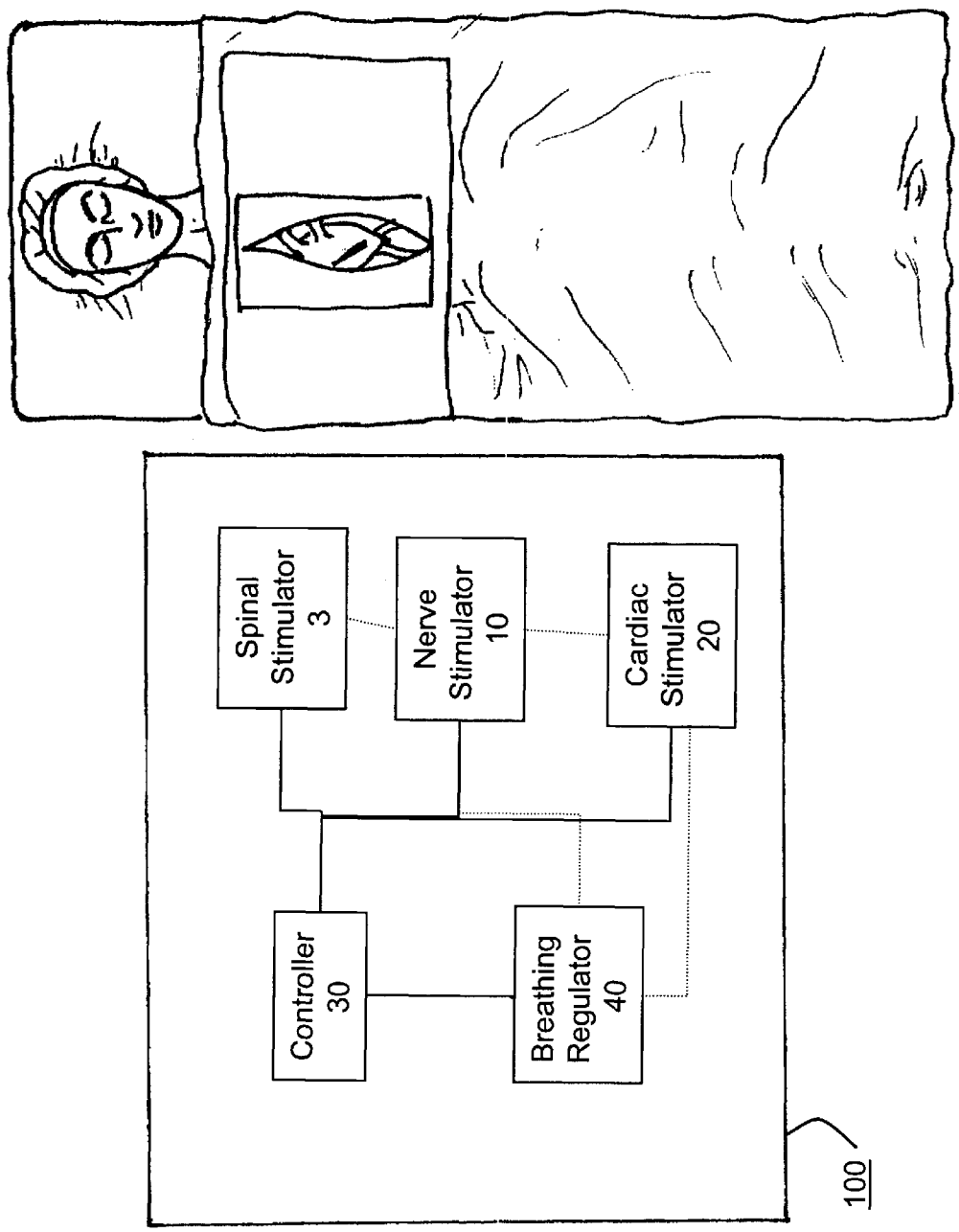
FIG. 1 is a schematic view of one embodiment of a system for stimulating the spinal cord during a medical procedure in accordance with the present invention.

FIG. 1 shows a schematic view of one embodiment of a system for performing a medical procedure in accordance with the present invention at 100. System 100 comprises a spinal cord stimulator 3, a nerve stimulator 10, and a cardiac stimulator 20. System 100 may also feature a controller 30 and a breathing regulator 40.

Spinal cord stimulator 3 may be an implantable pulse generator. Spinal cord stimulator 3 may also be any suitable stimulator that provides an electrical impulse to the spine. For example, spinal cord stimulator 3 may be a single lead or a suitable arrangement of electrical leads. Electrodes that may be used in spinal cord stimulator 3 may be, for example, cuff-type, needle-type, probe-type, transcutaneous, intracutaneous, patch-type, balloon-type, basket-type, umbrella-type, tape-type, screw-type, barb-type, metal, wire or suction-type electrodes. Guided or steerable catheter devices comprising electrodes may be used alone or in combination with the spinal cord stimulation electrodes. For example, a catheter comprising one or more wire, metal strips or metal foil electrodes or electrode arrays may be used. Application of an electrical stimulus to the spinal cord may include, but is not limited to bipolar and/or monopolar techniques.

All or a portion of spinal cord stimulator may be placed in any suitable manner for providing stimulation to the spine. Spinal cord stimulator 3 may be placed invasively or non-invasively. In one embodiment, all or a portion of spinal cord stimulator 3 is implanted adjacent the spine. Alternatively, all or a portion of spinal cord stimulator 3 may be implanted adjacent specific vertebrae. Electrical stimulation may be carried out on more than one area of the spinal cord simultaneously or sequentially. Alternatively, spinal cord stimulator 3 may be a guided or steerable electrode, which allows its position to be adjusted during the medical procedure. Different electrode positions are accessible through various access openings along the spinal cord. Spinal cord stimulator 3 may be positioned endoscopically through a percutaneous port, through an incision in the spine, placed on the skin or in combinations thereof. The present invention may include various electrodes, catheters and electrode catheters suitable for spinal cord stimulation. Other suitable placements of spinal cord stimulator 3 may be possible.

Spinal cord stimulator 3 may be powered by AC current, DC current or it may be battery powered either by a disposable or re-chargeable battery. Spinal cord stimulator 3 may be configured to synchronize activation and deactivation of breathing regulator 40 with vagal stimulation, thereby minimizing or eliminating unwanted heart or chest motion associated with the patient's breathing. Alternatively, spinal cord stimulator 3 may be placed so as to control the patient's lungs to minimize or eliminate unwanted heart motion. Spinal cord stimulator 3 may comprise a surgeon controlled switch box. A visual and/or audible signal used to alert a surgeon to the completion or resumption of spinal cord stimulation may be incorporated into spinal cord stimulator 3. For example, a beeping tone or flashing light that increases in frequency as the spinal stimulation period ends or begins may be used. A switch may also be incorporated in or on one of the surgeon's instruments, such as surgical site retractor, or any other location easily and quickly accessed by the surgeon for regulation of the spinal cord stimulator 3 by the surgeon. The switch may be, for example, a hand switch, a foot switch, or a voice-activated switch comprising voice-recognition technologies.

A visual and/or audible signal used to alert a surgeon to the completion or resumption of spinal cord stimulation may be incorporated into spinal cord stimulator 3. For example, a beeping tone or flashing light that increases in frequency as the spinal stimulation period should end or begin may be used.

Spinal cord stimulator 3 may be slaved to nerve stimulator 10 or cardiac stimulator 20. Software controlling spinal cord stimulator 3 may be designed to automatically stimulate the spine if nerve stimulator 10 or cardiac stimulator 20 is on.

System 100 may also include a nerve stimulator 10. In one embodiment, the nerve stimulator 10 may be used to electrically manipulate cardiac rhythm by stimulating the vagus nerve. This vagal stimulation may produce asystole (slowing or stopping of the heart's beating.) Once this induced asystole is stopped, i.e. once the vagal stimulation is stopped, the heart may be allowed to return to its usual cardiac rhythm. Alternatively, the heart may be paced with an electrical pacing system, thereby maintaining a normal cardiac output. Vagal stimulation, alone or in combination with electrical pacing, may be used selectively and intermittently to allow a surgeon to perform a medical procedure during intermittent periods of asystole.

It is known that stimulation of the vagus nerve can reduce the sinus rate, as well as prolong AV conduction time or, if stimulation energies are high enough, induce AV node block. Use of vagal nerve stimulation to treat supraventricular arrhythmias and angina pectoris is disclosed in the article "Vagal Tuning" by Bilgutay et al., Journal of Thoracic and Cardiovascular Surgery, Vol. 56, No. 1, July, 1968, pp. 71–82. It is also known that stimulation of the carotid sinus nerve produces a similar result, as disclosed in the article "Carotid Sinus Nerve Stimulation in the Treatment of Angina Pectoris and Supraventricular Tachycardia" by Braunwald et al., published in California Medicine, Vol. 112, pp. 41–50, March, 1970.

As set forth in "Functional Anatomy of the Cardiac Efferent Innervation" by Randall et al., in Neurocardiology, edited by Kulbertus et al, Futura Publishing Co., 1988, direct surgical excision of the fat pad associated with the SA node affects the functioning of the SA node without significantly affecting the AV node. Similarly, excision of the fat pad associated with the AV node affects functioning of the AV node without significantly affecting the SA node.

As set forth in the article "Parasympathetic Postganglionic Pathways to the Sinoatrial Node," Bluemel et al., Am. J. Physiol. 259, (Heart Circ. Physiol. 28) H1504-H1510, 1990, stimulation of the fat pad associated with the SA node results in slowing of the sinus rate without the accompanying prolongation of AV conduction time which normally results from vagal nerve stimulation. The article also indicates that stimulation of the fat pad associated with the AV node is believed to produce corresponding effects limited to the AV node, i.e., extension of the AV conduction time without concurrent slowing of the sinus rate.

As set forth in the article "Neural Effects on Sinus Rate and Atrial Ventricular Conduction Produced by Electrical Stimulation From a Transvenous Electrode Catheter in the Canine Right Pulmonary Artery" by Cooper et al., published in Circulation Research, Vol. 46, No. 1, January, 1980, pp. 48–57, the fat pads associated with both the AV node and the SA node may be stimulated by means of electrodes located in the right pulmonary artery. The results obtained include both a depression of the sinus rate and a prolongation of the AV conduction time in response to continuous stimulation at 2–80 Hz at up to 50 ma.

Generally in healthy individuals, the SA node functions as the pacemaker. Normal heart rhythm associated with the SA node is typically referred to as sinus rhythm. When the SA node fails, the AV node generally takes over creating a heart rate of approximately 35 to 60 beats per minute. Heart rhythm associated with the AV node is typically referred to as nodal rhythm. When the AV node itself is blocked or injured, a new even slower pacemaker site may form at the junction of the AV node and the His bundle. Heart rhythm associated with this junction is typically referred to as junctional escape rhythm. When this junction site is inhibited, the Purkinje fibers in the His bundle or below may act as a pacemaker creating a heart rate of approximately 30 beats per minute. Heart rhythm associated with the Purkinje fibers is typically referred to as idioventricular rhythm.

In one embodiment of the present invention, nerve stimulator 10 may be used to electrically manipulate cardiac rhythm by stimulating the carotid sinus nerve, the fat pad associated with the SA node, the fat pad associated with the AV node, the junction of the AV node and the His bundle and/or the Purkinje fibers.

In one embodiment of the present invention, nerve stimulator 10 is used alone or in combination with other heart rate inhibiting agents to temporarily stop or slow the beating heart, thereby eliminating or reducing heart motion and/or blood flow during a medical procedure. For example, the present invention may be used to eliminate or reduce motion in the anastomosis field during CABG procedures such that a facilitated anastomosis procedure may be performed safely and effectively. The number of occasions that the vagal nerve may be stimulated depends on the type of medical procedure to be performed. Likewise, the type of medical procedure to be performed will dictate the duration of the individual electrical stimulations.

Nerve stimulator 10 may be powered by AC current, DC current or it may be battery powered either by a disposable or re-chargeable battery. Nerve stimulator 10 may be configured to synchronize activation and deactivation of breathing regulator 40 with vagal stimulation, thereby minimizing or eliminating unwanted heart and chest motion associated with the patient's breathing. Nerve stimulator 10 may comprise a surgeon controlled switch box. A switch may be incorporated in or on one of the surgeon's instruments, such as surgical site retractor, or any other location easily and quickly accessed by the surgeon for regulation of the nerve stimulator 10 by the surgeon. The switch may be, for example, a hand switch, a foot switch, or a voice-activated switch comprising voice-recognition technologies.

A visual and/or audible signal used to alert a surgeon to the completion or: resumption of vagal nerve stimulation may be incorporated into nerve stimulator 10. For example, a beeping tone or flashing light that increases in frequency as the nerve stimulation period should end or begin may be used.

Nerve stimulator 10 may be slaved to cardiac stimulator 20 or cardiac stimulator 20 may be slaved to nerve stimulator 10. For example, the output of cardiac stimulator 20 may be off whenever the output of nerve stimulator 10 is on. Software controlling cardiac stimulator 20 may be designed to automatically commence cardiac pacing if the heart does not resume beating within a pre-determined interval after cessation of vagal nerve stimulation. In addition, the software controlling nerve stimulator 10 may be designed to automatically stop vagal nerve stimulation if the heart has been stopped for too long.

System 100 may also include cardiac stimulator 20 which may be used to stimulate the heart as desired. As with nerve stimulator 10, cardiac stimulator 20 may be intermittently stopped and started to allow the surgeon to perform individual steps of a medical procedure.

Cardiac stimulator 20 may be a conventional ventricular demand pacer or dual chamber (atrial-ventricular) pacer. Cardiac stimulator 20 may be powered by AC current, DC current or it may be battery powered either by a disposable or re-chargeable battery. Cardiac stimulator 20 may be configured to synchronize activation and deactivation of breathing regulator 40 with pacing, thereby minimizing or eliminating unwanted heart and chest motion associated with the patient's breathing. Cardiac stimulator 20 may be any conventional pacing device suitable for ventricular demand pacing and having leads electrically coupled to a switch box. Cardiac stimulator 20 may be combined in a single unit with a switch box. Cardiac stimulator 20 may comprise a surgeon controlled switch box. A switch may be incorporated in or on one of the surgeon's instruments, such as surgical site retractor, or any other location easily and quickly accessed by the surgeon for regulation of the cardiac stimulator by the surgeon. The switch may be, for example, a hand switch, a foot switch, or a voice-activated switch comprising voice-recognition technologies. A single switch may be used to regulate both cardiac stimulator 20 and nerve stimulator 10.

A visual and/or audible signal used to prepare a surgeon for the resumption of pacing may be incorporated into cardiac stimulator 20. For example, a beeping tone or flashing light that increases in frequency as the pacing period ends may be used. A single signaling method or device may be used for both cardiac stimulator 20 and nerve stimulator 10.

Spinal cord stimulator 3, nerve stimulator 10 and/or cardiac stimulator 20 may be slaved to a robotic system or a robotic system may be slaved to spinal cord stimulator 3, nerve stimulator 10 and/or cardiac stimulator 20. Breathing regulator 40 and other components may also be slaved to such a system. Computer and voice-controlled robotic systems that position and maneuver endoscopes and/or other surgical instruments for performing microsurgical procedures such as anastomoses through small incisions may be used by a surgeon to perform precise and delicate maneuvers. These robotic systems may allow a surgeon to perform a variety of microsurgical procedures including endoscopic CABG. Endoscopic CABG may allow multiple occluded coronary arteries to be bypassed without a thoracotomy or mini-thoracotomy. Heart valve repair and replacement may also be other surgical applications for these robotic systems. In general, robotic systems may include head-mounted displays which integrate 3-D visualization of surgical anatomy and related diagnostic and monitoring data, miniature high resolution 2-D and 3-D digital cameras, a computer, a high power light source and a standard video monitor.

System 100 may also include a breathing regulator 40. In one embodiment, the breathing regulator 40 may be used to stimulate the phrenic nerve in order to provide a diaphragmatic pacemaker. Breathing regulator 40 may comprise one or more electrodes for supplying electrical current to the phrenic nerve to control breathing during vagal and/or cardiac stimulation and/or destimulation. Electrodes used to stimulate the phrenic nerve may be, for example, non-invasive, e.g., clips, or invasive, e.g., needles or probes. The application of an electrical stimulus to the phrenic nerve may include, but is not limited to bipolar and/or monopolar techniques. Different electrode positions are accessible through various access openings, for example, in the cervical or thorax regions. Nerve stimulation electrodes may be positioned through a thoracotomy, sternotomy, endoscopically through a percutaneous port, through a stab wound or puncture, through a small incision, placed on the skin or in combinations thereof. The present invention may include various electrodes, catheters and electrode catheters suitable for phrenic nerve stimulation to control breathing.

Phrenic nerve stimulation electrodes may be intravascular, patch-type, balloon-type, basket-type, umbrella-type, tape-type, cuff-type, suction-type, screw-type, barb-type, bipolar, monopolar, metal, wire, endotracheal, endoesophageal, intravascular, transcutaneous or intracutaneous electrodes. Guided or steerable catheter devices comprising electrodes may be used alone or in combination with the nerve stimulation electrodes. For example, a catheter comprising one or more wire, metal strips or metal foil electrodes or electrode arrays may be used. The catheter may comprise, for example, a balloon that may be inflated with air or liquid to press the electrodes firmly against a vessel wall that lays adjacent the phrenic nerve.

Phrenic nerve stimulation electrodes may be oriented in any fashion along the catheter device, including longitudinally or transversely. Various techniques such as ultrasound, fluoroscopy and echocardiography may be used to facilitate positioning of the electrodes. If desired or necessary, avoidance of obstruction of blood flow may be achieved with notched catheter designs or with catheters which incorporate one or more tunnels or passageways.

In another embodiment, the breathing regulator 40 may comprise a connector which interfaces with a patient's respirator, and sends a logic signal to activate or deactivate the respirator to control breathing during vagal and/or cardiac stimulation and/or destimulation.

Figure 2:
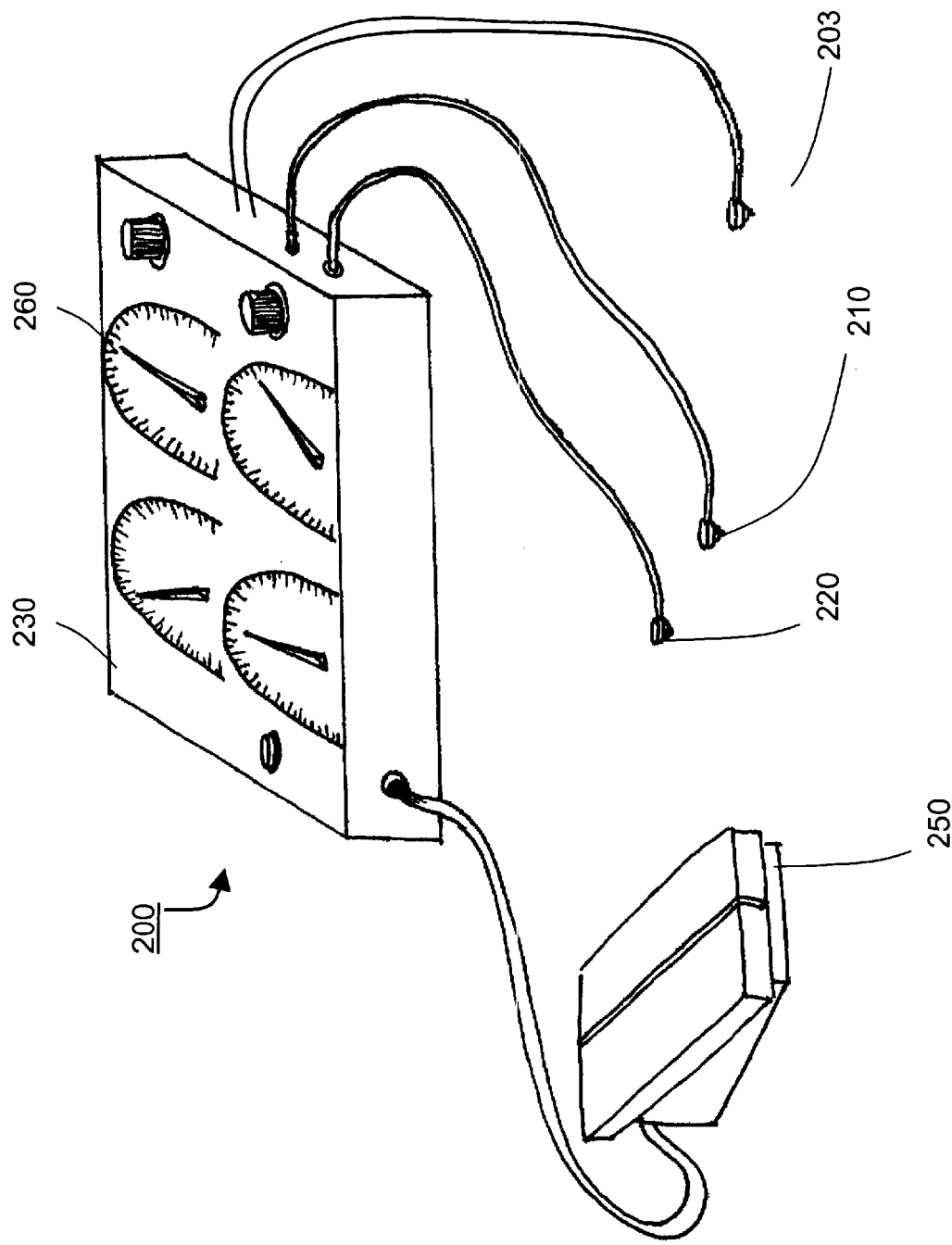
FIG. 2 is a schematic view of one embodiment of a medical device in accordance with the present invention.

FIG. 2 shows one embodiment of the present invention at 200. In this embodiment, the elements named above may be combined or connected to a control unit along with other components. The unit 200 may be used to coordinate the various elements. Unit 200 may incorporate a controller or any suitable processor 230.

Spinal cord stimulator 203 may be incorporated into unit 200. For example, FIG. 2 shows an electrode for spinal stimulation at 203.

Spinal stimulation electrodes 203 may be any suitable electrodes including: intravascular, transcutaneous, intracutaneous, patch-type, cuff-type, tape-type, screw-type, barb-type, metal, wire, balloon-type, basket-type, umbrella-type or suction-type electrodes. Guided or steerable catheter devices comprising electrodes may be used alone or in combination with the spinal cord stimulation electrodes 203. For example, a catheter comprising one or more wire, metal strips or metal foil electrodes or electrode arrays may be inserted adjacent the spine. Spinal stimulation electrodes 203 may be oriented in any fashion along the catheter device, including longitudinally or transversely. Various techniques such as ultrasound, fluoroscopy and echocardiography may be used to facilitate positioning of the electrodes.

In one embodiment of the present invention, the location of the electrodes 203 is chosen to elicit maximum stimulation to the spinal cord while preventing current spread to adjacent tissues. Furthermore, a non-conductive material such as plastic may be employed to sufficiently enclose the electrodes of all the configurations to shield them from the surrounding tissues and vessels, while exposing their confronting edges and surfaces for positive contact with the spinal cord.

Spinal electrode 203 may be in communication with a processor as shown in FIG. 2. The processor may thus be used to process the pulses being transmitted from spinal stimulator 203. The processor may store information about the pulses being generated. The processor may also be used to control or monitor the level or duration of spinal stimulation that occurs.

Unit 200 may also incorporate a nerve stimulator. For example, FIG. 2 shows an electrode for nerve stimulation at 210. Electrodes used to stimulate a nerve such as the vagal nerve may be, for example, non-invasive, e.g., clips, or invasive, e.g., needles or probes. The application of an electrical stimulus to the right or left vagal nerve may include, but is not limited to bipolar and/or monopolar techniques. Different electrode positions are accessible through various access openings, for example, in the cervical or thorax regions. Nerve stimulation electrodes 210 may be positioned through a thoracotomy, sternotomy, endoscopically through a percutaneous port, through a stab wound or puncture, through a small incision in the neck or chest, through the internal jugular vein, the esophagus, the trachea, placed on the skin or in combinations thereof. Electrical stimulation may be carried out on the right vagal nerve, the left vagal nerve or to both nerves simultaneously or sequentially. The present invention may include various electrodes, catheters and electrode catheters suitable for vagal nerve stimulation to temporarily stop or slow the beating heart alone or in combination with other heart rate inhibiting agents.

Nerve stimulation electrodes 210 may be endotracheal, endoesophageal, intravascular, transcutaneous, intracutaneous, patch-type, balloon-type, cuff-type, basket-type, umbrella-type, tape-type, screw-type, barb-type, metal, wire or suction-type electrodes. Guided or steerable catheter devices comprising electrodes may be used alone or in combination with the nerve stimulation electrodes 210. For example, a catheter comprising one or more wire, metal strips or metal foil electrodes or electrode arrays may be inserted into the internal jugular vein to make electrical contact with the wall of the internal jugular vein, and thus stimulate the vagal nerve adjacent to the internal jugular vein. Access to the internal jugular vein may be via, for example, the right atrium, the right atrial appendage, the inferior vena cava or the superior vena cava. The catheter may comprise, for example, a balloon that may be inflated with air or liquid to press the electrodes firmly against the vessel wall. Similar techniques may be performed by insertion of a catheter-type device into the trachea or esophagus. Additionally, tracheal tubes and esophageal tubes comprising electrodes may be used.

Nerve stimulation electrodes 210 may be oriented in any fashion along the catheter device, including longitudinally or transversely. Various techniques such as ultrasound, fluoroscopy and echocardiography may be used to facilitate positioning of the electrodes. If desired or necessary, avoidance of obstruction of blood flow may be achieved with notched catheter designs or with catheters which incorporate one or more tunnels or passageways.

In one embodiment of the present invention, the location of the electrodes 210 is chosen to elicit maximum bradycardia effectiveness while minimizing current spread to adjacent tissues and vessels and to prevent the induction of post stimulation tachycardia. Furthermore, a non-conductive material such as plastic may be employed to sufficiently enclose the electrodes of all the configurations to shield them from the surrounding tissues and vessels, while exposing their confronting edges and surfaces for positive contact with the vagal nerve or selected tissues.

Unit 200 may also incorporate a cardiac stimulator. For example, FIG. 2 shows an electrode for stimulation of the heart at 220. Cardiac electrodes 220 used to stimulate the heart may be, for example, non-invasive, e.g., clips, or invasive, e.g., needles or probes. Electrodes 220 may be positioned through a thoracotomy, sternotomy, endoscopically through a percutaneous port, through a stab wound or puncture, through a small incision in the chest, placed on the chest or in combinations thereof. The present invention may also use various electrodes, catheters and electrode catheters suitable for pacing the heart, e.g., epicardial, patch-type, intravascular, balloon-type, basket-type, umbrella-type, tape-type electrodes, suction-type, pacing electrodes, endotracheal electrodes, endoesophageal electrodes, transcutaneous electrodes, intracutaneous electrodes, screw-type electrodes, barb-type electrodes, bipolar electrodes, monopolar electrodes, metal electrodes, wire electrodes and cuff electrodes. Guided or steerable catheter devices comprising electrodes may be used alone or in combination with the electrodes.

Controller 230 may be used to gather information from spinal stimulation electrodes 203, nerve stimulation electrodes 210 and cardiac stimulation electrodes 220. Controller 230 may also be used to control the stimulation levels and stimulation duration of spinal stimulation electrodes 203, nerve stimulation electrodes 210 and cardiac stimulation electrodes 220. Controller 230 may also gather and process information from the various components of system 100. This information may be used to adjust stimulation levels and stimulation times of spinal stimulation electrodes 203, nerve stimulation electrodes 210 and cardiac stimulation electrodes 220.

Unit 200 may incorporate one or more switches to facilitate regulation of the various components by the surgeon. One example of such a switch is shown as foot pedal 250. The switch may also be, for example, a hand switch, or a voice-activated switch comprising voice-recognition technologies. The switch may be incorporated in or on one of the surgeon's instruments, such as surgical site retractor, or any other location easily and quickly accessed by the surgeon.

Unit 200 may also include a display 260. Unit 200 may also include other means of indicating the status of various components to the surgeon such as a numerical display, gauges, a monitor display or audio feedback. Unit 200 may also include one or more visual and/or audible signals used to prepare a surgeon for the start or stop of spinal cord stimulation, nerve stimulation and/or cardiac stimulation.

FIG. 3 shows a flow diagram of one embodiment of the present invention. The patient is prepared for a medical procedure at 500.

At this point, the spinal cord may be stimulated to alleviate the patient's pain (Block 505). The spinal cord may also be stimulated to control the patient's lungs or the functions of other organs. As seen in FIG. 3, spinal cord stimulation may occur throughout the entire procedure in a continuous or intermittent manner.

At Block 510, a nerve that controls the beating of the heart is stimulated. Such a nerve may be for example a vagal nerve. At Block 510, one or more of a variety of pharmacological agents or drugs may be delivered. These drugs may produce reversible asystole of a heart while maintaining the ability of the heart to be electrically paced.

A variety of pharmacological agents or drugs may also be delivered at other times during the procedure 500. These drugs may also produce reversible asystole of a heart while maintaining the ability of the heart to be electrically paced. Other drugs may be administered for a variety of functions and purposes as described below. Drugs may be delivered at any appropriate time during the medical procedure, for example, at the beginning of the procedure, intermittently during the procedure, continuously during the procedure or following the procedure.

Drugs, drug formulations or compositions suitable for administration to a patient during a medical procedure may include a pharmaceutically acceptable carrier or solution in an appropriate dosage. There are a number of pharmaceutically acceptable carriers that may be used for delivery of various drugs, for example, via direct injection, oral delivery, suppository delivery, transdermal delivery, epicardial delivery and/or inhalation delivery. Pharmaceutically acceptable carriers include a number of solutions, preferably sterile, for example, water, saline, Ringer's solution and/or sugar solutions such as dextrose in water or saline. Other possible carriers that may be used include sodium citrate, citric acid, amino acids, lactate, mannitol, maltose, glycerol, sucrose, ammonium chloride, sodium chloride, potassium chloride, calcium chloride, sodium lactate, and/or sodium bicarbonate. Carrier solutions may or may not be buffered.

Drug formulations or compositions may include antioxidants or preservatives such as ascorbic acid. They may also be in a pharmaceutically acceptable form for parenteral administration, for example to the cardiovascular system, or directly to the heart, such as intracoronary infusion or injection. Drug formulations or compositions may comprise agents that provide a synergistic effect when administered together. A synergistic effect between two or more drugs or agents may reduce the amount that normally is required for therapeutic delivery of an individual drug or agent. Two or more drugs may be administered, for example, sequentially or simultaneously. Drugs may be administered via one or more bolus injections and/or infusions or combinations thereof. The injections and/or infusions may be continuous or intermittent. Drugs may be administered, for example, systemically or locally, for example, to the heart, to a coronary artery and/or vein, to a pulmonary artery and/or vein, to the right atrium and/or ventricle, to the left atrium and/or ventricle, to the aorta, to the AV node, to the SA node, to a nerve and/or to the coronary sinus. Drugs may be administered or delivered via intravenous, intracoronary and/or intraventricular administration in a suitable carrier. Examples of arteries that may be used to deliver drugs to the AV node include the AV node artery, the right coronary artery, the right descending coronary artery, the left coronary artery, the left anterior descending coronary artery and Kugel's artery. Drugs may be delivered systemically, for example, via oral, transdermal, intranasal, suppository or inhalation methods. Drugs also may be delivered via a pill, a spray, a cream, an ointment or a medicament formulation.

Drugs may be delivered via a drug delivery device that may comprise a catheter, such as a drug delivery catheter or a guide catheter, a patch, such as a transepicardial patch that slowly releases drugs directly into the myocardium, a cannula, a pump and/or a hypodermic needle and syringe assembly. A drug delivery catheter may include an expandable member, e.g., a low-pressure balloon, and a shaft having a distal portion, wherein the expandable member is disposed along the distal portion. A catheter for drug delivery may comprise one or more lumens and may be delivered endovascularly via insertion into a blood vessel, e.g., an artery such as a femoral, radial, subclavian or coronary artery. The catheter can be guided into a desired position using various guidance techniques, e.g., flouroscopic guidance and/or a guiding catheter or guide wire techniques.

Drugs may be delivered via an iontophoretic drug delivery device placed on the heart. In general, the delivery of ionized drugs may be enhanced via a small current applied across two electrodes. Positive ions may be introduced into the tissues from the positive pole, or negative ions from the negative pole. The use of iontophoresis may markedly facilitate the transport of certain ionized drug molecules. For example, lidocaine hydrochloride may be applied to the heart via a drug patch comprising the drug. A positive electrode could be placed over the patch and current passed. The negative electrode would contact the heart or other body part at some desired distance point to complete the circuit. One or more of the electrodes may also be used as nerve stimulation electrodes 210 or as cardiac stimulation electrodes 220.

The two divisions of the autonomic nervous system that regulate the heart have opposite functions. First, the adrenergic or sympathetic nervous system increases heart rate by releasing epinephrine and norepinephrine. Second, the parasympathetic system also known as the cholinergic nervous system or the vagal nervous system decreases heart rate by releasing acetylcholine. Catecholamines such as norepinephrine (also called noradrenaline) and epinephrine (also called adrenaline) are agonists for beta-adrenergic receptors. An agonist is a stimulant biomolecule or agent that binds to a receptor.

Beta-adrenergic receptor blocking agents compete with beta-adrenergic receptor stimulating agents for available beta-receptor sites. When access to beta-receptor sites are blocked by receptor blocking agents, also known as beta-adrenergic blockade, the chronotropic or heart rate, inotropic or contractility, and vasodilator responses to receptor stimulating agents are decreased proportionately. Therefore, beta-adrenergic receptor blocking agents are agents that are capable of blocking beta-adrenergic receptor sites.

Since beta-adrenergic receptors are concerned with contractility and heart rate, stimulation of beta-adrenergic receptors, in general, increases heart rate, the contractility of the heart and the rate of conduction of electrical impulses through the AV node and the conduction system.

Drugs, drug formulations and/or drug compositions that may be used according to this invention may include any naturally occurring or chemically synthesized (synthetic analogues) beta-adrenergic receptor blocking agents. Beta-adrenergic receptor blocking agents or β-adrenergic blocking agents are also known as beta-blockers or β-blockers and as class II antiarrhythmics.

The term "beta-blocker" appearing herein may refer to one or more agents that antagonize the effects of beta-stimulating catecholamines by blocking the catecholamines from binding to the beta-receptors. Examples of beta-blockers include, but are not limited to, acebutolol, alprenolol, atenolol, betantolol, betaxolol, bevantolol, bisoprolol, carterolol, celiprolol, chlorthalidone, esmolol, labetalol, metoprolol, nadolol, penbutolol, pindolol, propranolol, oxprenolol, sotalol, teratolo, timolol and combinations, mixtures and/or salts thereof.

The effects of administered beta-blockers may be reversed by administration of beta-receptor agonists, e.g., dobutamine or isoproterenol.

The parasympathetic or cholinergic system participates in control of heart rate via the sinoatrial (SA) node, where it reduces heart rate. Other cholinergic effects include inhibition of the AV node and an inhibitory effect on contractile force. The cholinergic system acts through the vagal nerve to release acetylcholine, which, in turn, stimulates cholinergic receptors. Cholinergic receptors are also known as muscarinic receptors. Stimulation of the cholinergic receptors decreases the formation of cAMP. Stimulation of cholinergic receptors generally has an opposite effect on heart rate compared to stimulation of beta-adrenergic receptors. For example, beta-adrenergic stimulation increases heart rate, whereas cholinergic stimulation decreases it. When vagal tone is high and adrenergic tone is low, there is a marked slowing of the heart (sinus bradycardia). Acetylcholine effectively reduces the amplitude, rate of increase and duration of the SA node action potential. During vagal nerve stimulation, the SA node does not arrest. Rather, pacemaker function may shift to cells that fire at a slower rate. In addition, acetylcholine may help open certain potassium channels thereby creating an outward flow of potassium ions and hyperpolarization. Acetylcholine also slows conduction through the AV node.

Drugs, drug formulations and/or drug compositions that may be used according to this invention may include any naturally occurring or chemically synthesized (synthetic analogues) cholinergic agent. The term "cholinergic agent" appearing herein may refer to one or more cholinergic receptor modulators or agonists. Examples of cholinergic agents include, but are not limited to, acetylcholine, carbachol (carbamyl choline chloride), bethanechol, methacholine, arecoline, norarecoline and combinations, mixtures and/or salts thereof.

Drugs, drug formulations and/or drug compositions that may be used according to this invention may include any naturally occurring or chemically synthesized cholinesterase inhibitor. The term "cholinesterase inhibitor" appearing herein may refer to one or more agents that prolong the action of acetylcholine by inhibiting its destruction or hydrolysis by cholinesterase. Cholinesterase inhibitors are also known as acetylcholinesterase inhibitors. Examples of cholinesterase inhibitors include, but are not limited to, edrophonium, neostigmine, neostigmine methylsulfate, pyridostigmine, tacrine and combinations, mixtures and/or salts thereof.

There are ion-selective channels within certain cell membranes. These ion selective channels include calcium channels, sodium channels and/or potassium channels. Therefore, other drugs, drug formulations and/or drug compositions that may be used according to this invention may include any naturally occurring or chemically synthesized calcium channel blocker. Calcium channel blockers inhibit the inward flux of calcium ions across cell membranes of arterial smooth muscle cells and myocardial cells. Therefore, the term "calcium channel blocker" appearing herein may refer to one or more agents that inhibit or block the flow of calcium ions across a cell membrane. The calcium channel is generally concerned with the triggering of the contractile cycle. Calcium channel blockers are also known as calcium ion influx inhibitors, slow channel blockers, calcium ion antagonists, calcium channel antagonist drugs and as class IV antiarrhythmics. A commonly used calcium channel blocker is verapamil.

Administration of a calcium channel blocker, e.g., verapamil, generally prolongs the effective refractory period within the AV node and slows AV conduction in a rate-related manner, since the electrical activity through the AV node depends significantly upon the influx of calcium ions through the slow channel. A calcium channel blocker has the ability to slow a patient's heart rate, as well as produce AV block. Examples of calcium channel blockers include, but are not limited to, amiloride, amlodipine, bepridil, diltiazem, felodipine, isradipine, mibefradil, nicardipine, nifedipine (dihydropyridines), nickel, nimodinpine, nisoldipine, nitric oxide (NO), norverapamil and verapamil and combinations, mixtures and/or salts thereof. Verapamil and diltiazem are very effective at inhibiting the AV node, whereas drugs of the nifedipine family have a lesser inhibitory effect on the AV node. Nitric oxide (NO) indirectly promotes calcium channel closure. NO may be used to inhibit contraction. NO may also be used to inhibit sympathetic outflow, lessen the release of norepinephrine, cause vasodilation, decrease heart rate and decrease contractility. In the SA node, cholinergic stimulation leads to formation of NO.

Other drugs, drug formulations and/or drug compositions that may be used according to this invention may include any naturally occurring or chemically synthesized sodium channel blocker. Sodium channel blockers are also known as sodium channel inhibitors, sodium channel blocking agents, rapid channel blockers or rapid channel inhibitors. Antiarrhythmic agents that inhibit or block the sodium channel are known as class I antiarrhythmics, examples include, but are not limited to, quinidine and quinidine-like agents, lidocaine and lidocaine-like agents, tetrodotoxin, encainide, flecainide and combinations, mixtures and/or salts thereof. Therefore, the term "sodium channel blocker" appearing herein may refer to one or more agents that inhibit or block the flow of sodium ions across a cell membrane or remove the potential difference across a cell membrane. For example, the sodium channel may also be totally inhibited by increasing the extracellular potassium levels to depolarizing hyperkalemic values, which remove the potential difference across the cell membrane. The result is inhibition of cardiac contraction with cardiac arrest (cardioplegia). The opening of the sodium channel (influx of sodium) is for swift conduction of the electrical impulse throughout the heart.

Other drugs, drug formulations and/or drug compositions that may be used according to this invention may include any naturally occurring or chemically synthesized potassium channel agent. The term "potassium channel agent" appearing herein may refer to one or more agents that impact the flow of potassium ions across the cell membrane. There are two major types of potassium channels. The first type of channel is voltage-gated and the second type is ligand-gated. Acetylcholine-activated potassium channels, which are ligand-gated channels, open in response to vagal stimulation and the release of acetylcholine. Opening of the potassium channel causes hyperpolarization, which decreases the rate at which the activation threshold is reached. Adenosine is one example of a potassium channel opener. Adenosine slows conduction through the AV node. Adenosine, a breakdown product of adenosine triphosphate, inhibits the AV node and atria. In atrial tissue, adenosine causes the shortening of the action potential duration and causes hyperpolarization. In the AV node, adenosine has similar effects and also decreases the action potential amplitude and the rate of increase of the action potential. Adenosine is also a direct vasodilator by its actions on the adenosine receptor on vascular smooth muscle cells. In addition, adenosine acts as a negative neuromodulator, thereby inhibiting release of norepinephrine. Class III antiarrhythmic-agents also known as potassium channel inhibitors lengthen the action potential duration and refractoriness by blocking the outward potassium channel to prolong the action potential. Amiodarone and d-sotalol are both examples of class III antiarrhythmic agents.

Potassium is the most common component in cardioplegic solutions. High extracellular potassium levels reduce the membrane resting potential. Opening of the sodium channel, which normally allows rapid sodium influx during the upstroke of the action potential, is therefore inactivated because of a reduction in the membrane resting potential. The present invention may be combined with conventional CPB; the induced asystole as described by this invention may serve as a substitute for conventional cardioplegic arrest. For example, the combination of drugs and vagal stimulation may be used as a cardioplegic agent in a variety of medical procedures.

Drugs, drug formulations and/or drug compositions that may be used during according to this invention may comprise one or more of any naturally occurring or chemically synthesized beta-blocker, cholinergic agent, cholinesterase inhibitor, calcium channel blocker, sodium channel blocker, potassium channel agent, adenosine, adenosine receptor agonist, adenosine deaminase inhibitor, dipyridamole, monoamine oxidase inhibitor, digoxin, digitalis, lignocaine, bradykinin agents, serotoninergic agonist, antiarrythmic agents, cardiac glycosides, local anesthetics and combinations or mixtures thereof. Digitalis and digoxin both inhibit the sodium pump. Digitalis is a natural inotrope derived from plant material, while digoxin is a synthesized inotrope. Dipyridamole inhibits adenosine deaminase, which breaks down adenosine. Drugs, drug formulations and/or drug compositions capable of reversibly suppressing autonomous electrical conduction at the SA and/or AV node, while still allowing the heart to be electrically paced to maintain cardiac output may be used according to this invention.

In one embodiment, the cardiac asystole produced in accordance with the present invention is reversible, e.g., chemically such as by the administration of atropine or by natural forces. Beta-adrenergic stimulation or administration of calcium solutions may be used to reverse the effects of a calcium channel blocker such as verapamil. Agents that promote heart rate and/or contraction may be used in a preferred embodiment of the present invention. For example, dopamine, a natural catecholamine, is known to increase contractility. Positive inotropes are agents that specifically increase the force of contraction of the heart. Glucagon, a naturally occurring hormone, is known to increase heart rate and contractility. Glucagon may be used to reverse the effects of a beta-blocker since its effects bypass the beta-receptor. Forskolin is known to increase heart rate and contractility. As mentioned earlier, epinephrine and norepinephrine naturally increase heart rate and contractility. Thyroid hormone, phosphodiesterase inhibitors and prostacyclin, a prostaglandin, are also known to increase heart rate and contractility. In addition, methylxanthines are known to prevent adenosine from interacting with its cell receptors.

At Block 520, a medical procedure may be performed or begun. Such a procedure may be for example surgery on the heart. Alternatively, the procedure may be surgery performed on another organ of the body. Alternatively, the procedure may be a procedure such as delivery of a baby.

The term "medical procedure" may mean any one or more medical or surgical procedures such as, for example cardiac surgery, performed with or without cardiopulmonary bypass (CPB) circuits, heart valve repair, heart valve replacement, MAZE procedures, revascularization procedures, transmyocardial revascularization (TMR), percutaneous myocardial revascularization (PMR) procedures, CABG procedures, anastomosis procedures, non-surgical procedures, fluoroscopic procedures, beating heart surgery, vascular surgery, neurosurgery, brain surgery, electrophysiology procedures, diagnostic and therapeutic procedures, ablation procedures, ablation of arrhythmias, endovascular procedures, treatment of the liver, spleen, heart, lungs, and major blood vessels, aneurysm repair, imaging procedures of the heart and great vessels, CAT scans or MRI procedures, pharmacological therapies, drug delivery procedures, gene therapies, cellular therapies, cancer therapies, radiation therapies, genetic, cellular, tissue and/or organ manipulation or transplantation procedures, coronary angioplasty procedures, placement or delivery of coated or noncoated stents, atherectomy procedures, atherosclerotic plaque manipulation and/or removal procedures, birthing procedures, procedures where bleeding needs to be precisely controlled, procedures that require precise control of cardiac motion and/or bleeding.

When the medical procedure comprises one or more medical devices, e.g., coated stents, these devices may be coated with one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand). Biological agents may be found in nature (naturally occurring) or may be chemically synthesized.

The medical procedure may be non-invasive, minimally invasive and/or invasive. The medical procedure may entail a port-access approach, a partially or totally endoscopic approach, a sternotomy approach or a thoracotomy approach. The medical procedure may include the use of various mechanical stabilization devices or techniques as well as various robotic or imaging systems.

In one method, the heart may be temporarily slowed or intermittently stopped for short periods of time to permit the surgeon to accomplish the required surgical task and yet still allow the heart itself to supply blood circulation to the body. For example, stimulation of the vagus nerve in order to temporarily and intermittently slow or stop the heart is described in U.S. Pat. No. 6,006,134 entitled "Method and Device for Electronically Controlling the Beating of a Heart Using Venous Electrical Stimulation of Nerve Fibers", Dec. 21, 1999, to inventors Hill and Jonkman. This patent is assigned to Medtronic, Inc. and is incorporated herein by reference.

After a time, the medical procedure or one phase of the procedure is completed at 520. After some phase of the medical procedure is performed, cardiac contractions are allowed to occur (Block 530). Cardiac contractions may need to occur intermittently during the procedure to ensure adequate blood flow. In one embodiment, the stimulation from the nerve stimulator 10 is stopped or slowed enough to allow the heart to contract. For example, the vagal nerve stimulation is removed, thereby allowing cardiac contractions to occur.

In another embodiment, the heart may be stimulated to ensure that cardiac contractions occur (Block 535). For example, cardiac stimulator 20 may be used to apply pacing pulses to the heart to encourage the heart to contract normally. In particular, the pacing pulses may be applied to the ventricle as is well known in the field.

The present invention permits the heart to be stilled for selected and controllable periods of time in order to permit a medical procedure, such as cardiac surgery or other surgery, to be performed. While such a period of stillness is desired, it must not last too long, otherwise insufficient blood and oxygen is delivered to organs. Thus, it is necessary to have the periods when the heart is beating (Blocks 530, 535).

If additional medical procedures or additional stages of medical procedures need to be performed, the heart may again be stilled using the methods of stilling the heart described above. Therefore from Block 530 or Block 535, the method may be repeated (loop designated by Block 540). For example, the heart may again be prevented from contracting by stimulation of the vagal nerve (Block 510). Additional drugs may be delivered or the drugs previously administered may continue to be administered.

Additional steps of the medical procedure or additional medical procedures may be performed (Block 520) while the heart is still. Then, this stage of stillness may be followed by another stage when the stimulation is removed (Block 530) and the heart is allowed to contract. Again, the heart may be stimulated to encourage contractions (Block 535).

This cycle may be repeated until the procedure, such as the surgery, is completed. After the procedure is completed, step 535 may be performed until the heart is beating normally. In addition, one or more of a variety of pharmacological agents or drugs may be delivered or may continue to be delivered after the procedure is completed.

For example, a surgical procedure at 520 may require several stitches to be made by the surgeon. The surgeon may stimulate the vagal nerve at 510 to stop the heart. Then the surgeon may make the first stitch at 520. The surgeon may then reduce or halt stimulation at 530 and allow the heart to contract. The surgeon may also pace the heart at 535. Then at 540, the surgeon may return to 510 to inhibit contractions of the heart. At 520, the surgeon will then make the second stitch. This process may be repeated (the loop designated by 540 may be repeated) until all the required stitches have been made.

In one embodiment, after the surgery is completed, step 535 is performed until the heart is beating normally. Finally, after the patient's pain should be sufficiently tolerable, the spinal stimulation may be terminated (Block 545). Alternatively, the spinal cord stimulator may be permanently or semi-permanently implanted in the patient.

FIG. 4 is a timeline illustrating one embodiment of the relationship between spinal cord stimulation, vagal nerve stimulation and cardiac stimulation.

Point 610 indicates a point before the medical procedure has begun. At this point 610, both nerve stimulation and cardiac stimulation are off. At point 610, the heart is beating regularly. Stimulation to the spinal cord may be off at point 610 or may be begun at this point.

Then nerve stimulation is turned on to inhibit beating of the heart. During phase 601, the vagal nerve stimulation is on and the cardiac stimulation is off. This is the condition of the two types of stimulation at step 520 described above. In one embodiment, shown in FIG. 3 spinal cord stimulator 3 is on throughout the entire procedure. Alternatively, spinal cord stimulation may be turned on intermittently during the procedure.

Point 611 is a representative point during phase 601. At point 611, the contractions of the heart are stilled or substantially slowed. Spinal cord stimulation may still occur at point 611.

During phase 602 the vagal stimulation is turned off (as described at step 530) and the cardiac stimulation may be turned on (as described at 535). Point 612 is a representative point during phase 602. At point 612, the contractions are allowed and/or may be induced. In one embodiment, spinal cord stimulation is on during phase 602.

During phase 603, the vagal nerve stimulation is again turned on and the cardiac stimulation is turned off. During phase 604 the vagal stimulation is again turned off and the cardiac stimulation may again be turned on.

The method of the present invention may be repeated as necessary until a point is reached, represented by point 615, when the necessary medical procedures are completed. At this point 615, nerve stimulation is off although cardiac stimulation may be left on in order to pace the heart to its normal rhythm. At point 615, spinal cord stimulation may be turned off as described at Block 545. Alternatively, spinal cord stimulation may continue as needed.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A system for performing a medical procedure, comprising:

a spinal stimulator to reduce pain during the medical procedure;

a nerve stimulator in communication with the spinal stimulator to inhibit beating of the heart; and a cardiac stimulator in communication with the spinal stimulator to stimulate beating of the heart.

2. The system of claim 1 further comprising:

drug delivery means for delivering at least one drug during the medical procedure.

3. The system of claim 1 wherein the drug delivery means are selected from the group consisting of:

a spray, a cream, an ointment, a medicament, a pill, a patch, a catheter, a cannula, a needle and syringe, a pump, and an iontophoretic drug delivery device.

4. The system of claim 1 wherein the nerve stimulator stimulates a parasympathetic nerve fiber.

5. The system of claim 1 wherein the nerve stimulator stimulates a nerve selected from the group consisting of:

a vagal nerve, a carotid sinus nerve, a fat pad.

6. The system of claim 1 wherein the spinal stimulator comprises at least one electrode.

7. The system of claim 6 wherein the electrode is selected from the group consisting of:

spinal stimulation electrodes, balloon-type electrodes, basket-type electrodes, umbrella-type electrodes, suction-type electrodes, guided catheters, guided electrodes, steerable catheters, and steerable electrodes.

8. The system of claim 1 wherein the nerve stimulator comprises at least one electrode.

9. The system of claim 8 wherein the electrode is selected from the group consisting of:

nerve stimulation electrodes, endotracheal electrodes, endoesophageal electrodes, intravascular electrodes, transcutaneous electrodes, intracutaneous electrodes, balloon-type electrodes, basket-type electrodes, umbrella-type electrodes, tape-type electrodes, suction-type electrodes, screw-type electrodes, barb-type electrodes, bipolar electrodes, monopolar electrodes, metal electrodes, wire electrodes, patch electrodes, cuff electrodes, clip electrodes, needle electrodes and probe electrodes.

10. The system of claim 1 wherein the cardiac stimulator comprises at least one electrode.

11. The system of claim 9 wherein the electrode is selected from the group consisting of:

cardiac stimulation electrodes, clip electrodes, needle electrodes, probe electrodes, pacing electrodes, epicardial electrodes, patch electrodes, intravascular electrodes, balloon-type electrodes, basket-type electrodes, tape-type electrodes, umbrella-type electrodes, suction-type electrodes, endotracheal electrodes, endoesophageal electrodes, transcutaneous electrodes, intracutaneous electrodes, screw-type electrodes, barb-type electrodes, bipolar electrodes, monopolar electrodes, metal electrodes, wire electrodes and cuff electrodes.

12. The system of claim 1 further comprising:

a processor operatively connected to the spinal stimulator, the nerve stimulator and the cardiac stimulator.

13. The system of claim 12 wherein the processor processes output from the spinal stimulator and adjusts output from the nerve stimulator based on output from the spinal stimulator.

14. The system of claim 12 wherein the processor processes output from the spinal stimulator and adjusts output from the cardiac stimulator based on output from the spinal stimulator.

* * * * *